(12) United States Patent
Yang et al.

(10) Patent No.: US 6,965,038 B2
(45) Date of Patent: Nov. 15, 2005

(54) ACYLATED AMINOTHIOL COMPOUND

(75) Inventors: Teng-Kuei Yang, Taichung (TW);
Nan-Kuang Chen, Taichung (TW); To Liu, Taichung (TW)

(73) Assignee: National Chung-Hsing University, Taichung (TW)

( * ) Notice: Subject to any disclaimer, the term of this patent is extended or adjusted under 35 U.S.C. 154(b) by 44 days.

(21) Appl. No.: 10/650,020

(22) Filed: Aug. 26, 2003

(65) Prior Publication Data

US 2004/0049033 A1 Mar. 11, 2004

Related U.S. Application Data

(62) Division of application No. 10/039,557, filed on Jan. 8, 2002, now Pat. No. 6,861,536.

(51) Int. Cl.[7] .............................................. C07D 207/04
(52) U.S. Cl. ..................... 548/570; 548/574; 548/571
(58) Field of Search ................. 548/571, 570, 548/574; 558/250; 564/440

(56) References Cited

PUBLICATIONS

Nishimura et al., 1965, CAS: 62:8904.*
Kossenjans et al., 1999, CAS:131:350834.*
Wipf et al., 1998, CAS: 129:289723.*
Kang et al., 1996, CAS: 126:131036.*
Jin et al., 1996, 126:103872.*
Kang et al., 1994, CAS: 123:142957.*
Poelert et al., 1994, CAS: 121:280925.*

* cited by examiner

*Primary Examiner*—Rita Desai
*Assistant Examiner*—Robert Shiao
(74) *Attorney, Agent, or Firm*—Charles E. Baxley

(57) ABSTRACT

The present invention discloses an acylated derivative of an aminothiol compound having a general formula II wherein $R^1$–$R^4$ and $R^6$ are substitutable ligands. Such compounds can perform as superior catalysts in asymmetric addition reactions of organic zinc and aldehyde. According to the present invention, only less than 0.02% of the acylated derivative is needed to obtain high enantioselectivity over 99% enantiomeric excess.

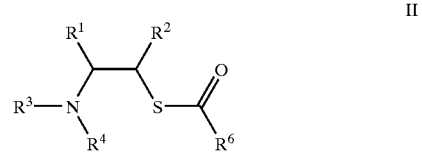

II

5 Claims, 1 Drawing Sheet

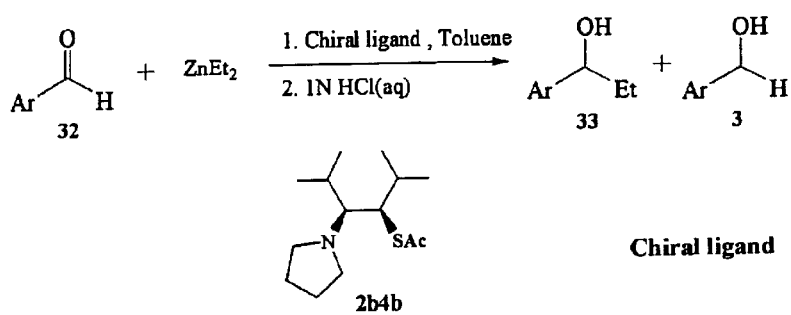
Table 1: The Ratios of Substrate to Chiral Ligands (S/C)
| Entry[a] | Ligand | S/L | Conversion (%) | 33 : 34 | e.e.(%) |
|---|---|---|---|---|---|
| 11 | 2b4b | 10000 | 68 | 1 : 0.015 | 96.0 (R) |
| 12 | 2b4b | 5000 | 81 | 1 : 0.005 | 97.7 (R) |
| 13 | 2b4b | 2000 | 82 | 1 : 0.005 | 98.1 (R) |
| 14 | 2b4b | 1000 | 100 | 1 : 0 | 99.3 (R) |
| 15 | 2b4b | 200 | 100 | 1 : 0 | 99.5 (R) |
| 16 | 2b4b | 100 | 100 | 1 : 0 | 99.5 (R) |
| 17 | 2b4b | 20 | 100 | 1 : 0 | 99.6 (R) |
| 18 | 2b4b | 10 | 100 | 1 : 0 | 99.6 (R) |
| 19 | 2b4b | 5 | 100 | 1 : 0 | 99.7 (R) |
| 20 | 2b4b | 2 | 100 | 1 : 0 | 99.6 (R) |
[a] All of the above reactions used benzaldehyde as the substrate, toluene as the solvent. [b] 3.7 eq. of Et$_2$Zn was used. [c] The reaction were carried at -20°C for 12hrs. [d] S/C was the ratio between the substrate and chiral ligand.

ACYLATED AMINOTHIOL COMPOUND

PATENT CASE TEXT

This application is a divisional of application Ser. No. 10/039,557, filed on Jan. 8, 2002 now U.S. Pat. No. 6,861,536, and for which priority is claimed under 35 U.S.C.. sctn.120.

BACKGROUND OF THE INVENTION

1. Field of the Invention

The present invention relates to an acylated aminothiol compound which performs as a superior catalyst in an asymmetric addition reaction of organic zinc and aldehyde.

2. Description of the Related Technology

For preparing secondary alcohols, one of the most important methods is to react organic zinc with aldehyde in addition reactions. In order to accelerate this reaction, chiral aminoalcohols are usually added as ligands to combine with organic zinc. Such chiral aminoalcohol create an asymmetric reaction environment, so that one of the produced chiral secondary alcohols is produced more than its stereoisomer, i.e., the asymmetric addition reactions. Apparently, the crux of obtaining a high chemical yield as well as enantioselectivity in the above reactions is to select proper chiral compounds which can provide excellent asymmetric environment for catalytical process.

Though many chiral compounds used in the addition reactions regarding organic zinc and aldehyde can achieve good enantioselectivity, however, these compounds have to be added at an amount at least 1% of the main reactants, and usually around 20%. Additionally, the enantioselectivity always decays with decreasing amount of the chiral ligands used. In general, the enantioselectivity is reduced below 90% enantiomeric excess (e.e.) when the chiral ligands are descended under 5%, so that most of above reactions are not good enough for industrial usage.

Aminoalcohols with optical activity, such as N,N-dibutylnorepheedine, are frequently applied to accelerating the asymmetric addition reactions of organic zinc and aldehyde as chiral ligand catalysts. By adding aminoalcohols, enantioselectivity of the above reactions can be reached as high as 99% e.e., but an amount 10–20% of chiral aminoalcohols is need. Therefore, it's an important issue how to reduce the necessary amount of the chiral ligands used in the catalysis, so that it can be an economically efficient process

SUMMARY OF THE INVENTION

The object of the present invention is to provide acylated aminothiol compounds with two chiral centers, which can increase enantioselectivity of asymmetric addition reactions of organic zinc and aldehyde.

The acylated aminothiol compounds of the present invention have a general formula II;

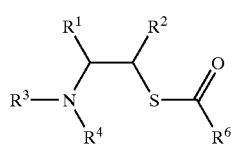

II wherein $R^1$ is aryl or alkyl of C1–C9;

$R^2$ is aryl or alkyl of C1–C9;

$R^3$ is alkyl of C1–C9;

$R^4$ is alkyl of C1–C9; or $R^3$, $R^4$ and N form a cycle; and $R^6$ is H or alkyl of C1–C6.

According to the present invention, the acylated aminothiol compounds can perform as superior catalysts in asymmetric addition reactions wherein organic zinc and aldehyde are involved, In such reactions, though the catalysts are added only 0.1% or even 0.02%, enantioselectivity higher than 99% e.e. can always be obtained. So that such catalyses are economically useful for industries.

DETAILED DESCRIPTION OF THE PREFERRED EMBODIMENTS

Acylated aminothiol compounds of the present invention have a general formula II,

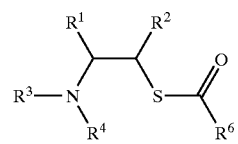

II wherein $R^1$ is aryl or alkyl of C1–C9;

$R^2$ is aryl or alkyl of C1–C9;

$R^3$ is alkyl of C1–C9;

$R^4$ is alkyl of C1–C9; or $R^3$, $R^4$ and N can form a three-to-eight-membered heterocycle;

and $R^6$ can be H or alkyl of C1–C6.

A typical method for preparing the above compounds and application thereof are as follows:

1. Preparing the Ligand

A typical compound of the present invention can be obtained according to the following scheme,

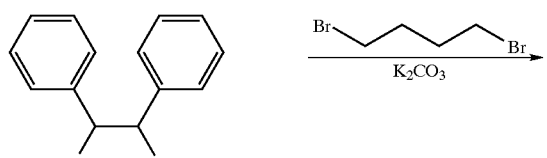

(IV)

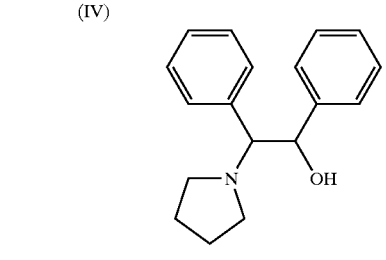

(III)

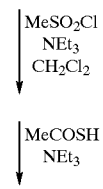
MeSO$_2$Cl
NEt$_3$
CH$_2$Cl$_2$

MeCOSH
NEt$_3$

-continued (II-1)

The compound of formula II-1 is produced by reacting (1R, 2S)-(−)-1,2-diphenyl-2-aminoethanol, i.e., the compound of formula IV, with 1,4-dibromobutane and potassium carbonate to produce the compound of formula III with the cyclic structure as morpholine. The procedures are as follows:

S21: The compound of formula III is dissolved in dichloromethane under nitrogen, then triethylamine is injected therein, and the temperature is reduced to 0° C.

S22: MeSO$_2$Cl dissolved in dichloromethane is dropwisely added into the solution obtained in S21 through a funnel.

S23: After the above solution has completely reacted by stirring for two hours, the aliquote is concentrated by reducing pressure through a vacuum pump, benzene is added therein under nitrogen, and the mixture is heated and refluxed.

S24: Thiolacetic acid and triethylamine are dissolved in benzene and then injected into the mixture of S23.

S25: After the above mixture has completely reacted by stirring for eight hours, H$_2$O is added therein to terminate the reaction, and the mixture is extracted with dichloromethane for three times.

S26: Anhydrous Na$_2$SO$_4$ is added into the organic layer obtained in S25 to absorb H$_2$O, which is then filtered and concentrated by reducing pressure through vacuum pump to obtain crude product.

S27: The crude product is purified by column chromatography (Silica gel, eluent is n-Hexane: EtOAc: Et$_3$N= 100:1:1) to obtain a yellow liquid, i.e., the compound of formula II-1.

2. Application of the Present Invention

In order to confirm that high enantioselectivity can be obtained from the present invention, the acylated aminothiol compound, having a formula 2b4b as shown in Table 1, is provided to perform the reaction. The addition reaction of organic zinc and aldehyde can be shown as the following scheme.

The above scheme includes steps of:

S31: The ligand of formula 2b4b (0.03 g, 0.1 mmol) and a dried magnetic stirrer are added into a dried flask.

S32: The flask is sealed and vacuumed to remove moisture and then filled with nitrogen, and then diethylzinc (1.10 mL, 1.2 mmol) is added therein at room temperature and stirred for two hours.

S33: The temperature is adjusted to −20° C., and benzaldehyde (0.11 mL, 1.0 mmol) is added therein and stirred for 12 hours.

S34: 1N aqueous HCl (1 mL) is added into the above solution to terminate the reaction.

S35: The solution of S34 is extracted with acetyl acetate (20 mL), wherein the organic layer is collected and dehydrated with anhydrous MgSO$_4$, and then the mixture is filtered, and the filtrate is concentrated by reducing pressure through an air pump to obtain crude product.

S36: The crude product is purified by column chromatography (Silica gel, eluent is n-Hexane: EtOAc=10:1).

The results are listed in Table 1, in which only few values of enantioselectivity are lower than 99% e.e. when the amount of these ligands is 0.02%. Additionally, when the amount of these ligands is 0.1%, all values of enantioselectivity are higher than 99% e.e.

Obviously, the acylated aminothiol compounds in accordance with the present invention are superior than the catalysts existing in the literature for the asymmetric addition reactions of organic zinc to aldehyde. In such reactions, though the catalysts are added only 0.1% or even 0.02%, enantioselectivity higher than 99% e.e. are always obtained. Therefore, acylated aminothiol compounds in the present invention are indeed very economic for applying the above asymmetric reactions to industries.

Similarly, the acylated aminothiol compounds in the present invention can be provided as chiral ligands to react with other organic metals, for example, Cu, Ti, etc., to form organometal complexes. These complexes can also react with carbonyl such as aldehyde and ketone, to produce alcohol in the asymmetric addition reactions.

It should be noticed that the above embodiments are only used for explaining the present invention, but not limiting the scope.

What is claimed is:

1. An acylated aminothiol compound, having a general formula II,

II $R^1$ is aryl or alkyl of C1–C9;
$R^2$ is alkyl of C1–C9;
$R^3$, $R^4$ and N form a five-membered heterocycle pyrrolidine; and
$R^6$ is H.

2. The acylated aminothiol compound as claimed in claim 1, which are chiral ligands capable of reacting with organic metal compounds to form metal complexes and then react with carbonyl compounds to produce alkylmetal in asymmetric addition reactions.

3. The acylated aminothiol compound as claimed in claim 2, wherein said carbonyl compound is aldehyde.

4. The acylated aminothiol compound as claimed in claim 2, wherein said carbonyl compound is ketone.

5. The acylated aminothiol compound as claimed in claim 2, wherein said metal is Zn, Cu, or Ti.

* * * * *